US 6,316,602 B1
(12) United States Patent
Lipps

(10) Patent No.: US 6,316,602 B1
(45) Date of Patent: Nov. 13, 2001

(54) BETA TAIPOXIN AS A CELL GROWTH FACTOR AND METHOD

(76) Inventor: Binie V. Lipps, 4509 Mimosa Dr., Bellaire, TX (US) 72401

( * ) Notice: Subject to any disclaimer, the term of this patent is extended or adjusted under 35 U.S.C. 154(b) by 0 days.

(21) Appl. No.: 08/237,129

(22) Filed: May 3, 1994

(51) Int. Cl.$^7$ .................................................. A61K 38/18
(52) U.S. Cl. .......................................... 530/399; 530/350
(58) Field of Search ...................................... 530/399, 350

(56) References Cited

PUBLICATIONS

Harris et al., "Protein purification methods", IRL Press, pp. 175–215, 1989.*
Siigur et al., Comp. Biochem. Physiol., vol. 83B(3), pp 621–25, 1986.*
Banks et al., Biochem J., vol. 108, pp. 157 to 158, 1968.*
Lawman et al., Exp. Mol. Pathol., vol. 43(3), pp. 274–281, 1985.*
Lind, Eur. J. Biochem., vol. 128, pp. 71–75, 1982.*
Scopes, "Protein Purification", Third Edition, Springer–Verlag pp. 154–158, 1993.*
Fohlman et al., Eur. J. Biochem., vol. 68, pp. 457–469 1976.*
Lind, Eur. J. Biochem, vol. 128(1), p. 71–75, 1982.*
J. Fohlman, D. Eaker, E. Karlsson and S. Thesleff, Taipoxin, an Extremely Potent Presynaptic Neurotoxin from the Venom of the Australian Snake Taipan, Eur. J. Biochem 68, 457–469 (1976).
P. Lind, Amino–Acid Sequence of the B1 Isosubunit of Taipoxin . . . Eur. J. Biochem, 128; 71–75 (1982).
G. S. Schultz et al., Epithelial Wound Healing Enhanced by Transforming Growth Factor, Science, 235, 350–352, (1987).
A. Wells, J.B. Welsh, C.S. Lazar, H.S. Wiley, G.N. Gili & M.G. Rosenfeld, Ligand–Induced Transformation by a Non-internalizing Epidermal Growth Factor Receptor, Science, 247, 962–964, (1990).
A. Buckley, J.M. Davidson, C.D. Kamerath, T.B. Wolf & S.C. Wooward, Release of Epidermal Growth Factor Accelerates Repair, Proc. Natl Acad Sci. USA 82, 7340–7344, (1985).
J.F. Rubin et al., Purification & Characterization of a Newly Identified Growth Factor Specific for Epithelial Cells, Proc. Natl. Acad. Sci. USA 86, 802–806 (1989).
G.L. Brown et al., Enhancement of Epidermal Regeneration by Biosynthetic Epidermal Growth Factor, J.Exp. Med. The Rockefeller University Press, 163, 1319–1324, (1986).

* cited by examiner

*Primary Examiner*—Chhaya D. Sayala
(74) *Attorney, Agent, or Firm*—John R Casperson

(57) ABSTRACT

A peptide containing a sequence for the first fifteen amino acids from the N-terminal of Asn-Leu-Val-Glu-Phe-Gly-Lys-Met-Ile-Glu-Cys-Ala-Ile-Arg-Asn is used in a cell culture medium to promote cell growth in vitro and in the treatment of wounds. A method of preparation of the peptide is also described.

9 Claims, 3 Drawing Sheets

BETA TAIPOXIN AS A CELL GROWTH FACTOR AND METHOD

FIELD OF THE INVENTION

The present invention relates to the discovery of non-toxic beta taipoxin as a cell growth factor and a potent mitogen from poisonous snake venom. Said composition consists of a polypetide of beta taipoxin having molecular weight approximately 14,000 daltons and is free of toxic effects.

BACKGROUND OF THE INVENTION

Taipoxin as a whole intact molecule isolated from the venom of the Australian taipan *Oxyuranus s. scutellatus* is the most lethal neurotoxin. The whole molecule of taipoxin is a complex, composed of three subunits designated as alpha, beta and gamma, having molecular weight 45,6000 daltons. Taipoxin can not be isolated by ion-exchange chromatography, since ion exchangers tend to dissociate the active toxin complex. The major lethality of taipoxin is due to the very basic alpha subunit. The molecular weights of alpha, beta and gamma subunits of taipoxin are 13,750, 13,473 and 18,354 daltons respectively.

To date numerous growth factors have been isolated from various sources, and have been characterized. To name a few, epidermal growth factor (EGF), fibroblast growth factor (FGF), nerve growth factor (NGF) and platelet derived growth factor (PDGF).

It is an object of this invention that the beta taipoxin as a cell growth factor can be used to grow cells in serum free medium. Routinely, cells are grown in the presence of 5 to 20% fetal bovine serum (FBS) for research or production. The purification of products derived from cells grown in serum containing medium is a cumbersome task and furthermore, fetal bovine serum is the most expensive ingredient of the medium. A mitogen like cell growth factor will provide serum free environment with adequate cell proliferation.

A further object of this invention is to provide non-toxic beta taipoxin having mitogenic activity as a composition for the promotion of rapid bum and wound healing. In the case of cuts, surgical incisions, and abrasions to lessen the risk of infection and to shorten recovery time.

SUMMARY OF THE INVENTION

Cell growth factor has been isolated as the beta subunit of taipoxin by fractionating *Oxyuranus s. scutellatus* snake venom by high pressure liquid chromatography. After testing for mitogenic activity in all fractions, the mitogenic activity was revealed in one of the fractions. Cell growth factor is a beta taipoxin, which is a non-toxic fraction of snake venom and is a potent mitogen. Cell growth factor has been isolated from the venom of the poisonous snake species *Oxyuranus s. scutellatus*.

The concentration of 0.1 $\mu$/ml of the beta taipoxin non-toxic subunit becomes a cell growth factor and in serum free medium it gives growth equivalent to medium containing 10% serum for a wide range of cells. Cell growth factor is a beta taipoxin peptide having a molecular weight 14,000 daltons.

In vivo experiments proved that beta taipoxin as a cell growth factor acts as a potent mitogen. The cut portion of mouse hip skin healed much faster when cell growth factor was applied as compared to the control counter part. Cell growth factor helped heal a chronic foot wound of a friend. Cell growth factor is claimed as wound healer and its use may be extended to treat burns.

DETAILED DESCRIPTION OF THE INVENTION

The cell growth factor consists essentially of a peptide of which first 15 amino acid sequence is: Asp-Leu-Val-Glu-Phe-Gly-Lys-Met-Ile-Glu-Cys-Ala-Ile-Arg-Asn, which is exactly similar to beta taipoxin. For convenience this sequence is referred herein as SEQ ID No: 1. It is believed that any peptide having the partial amino acid sequence SEQ ID No: 1 exhibits substantial utility as a cell growth promoter, a potent mitogen, regardless whether it is synthesized or derived from natural sources. By the term, cell growth factor, we mean a substance whose presence produces a substantial mitogenic effect on various types of cells, and that the mitogenic effect is indicated, by an increase in cell growth or by a decreased duplication time of various types of cells.

Preferably, the peptide cell growth factor contains the first fifteen amino acids at N-terminal as given by SEQ ID No: 1, and has a molecular weight of about 14,000 daltons revealed by electrophoresis which is similar to beta taipoxin. In addition, cell growth factor is water soluble and stable at 4° C. storage for its biological activity. Cell growth factor is stable at room temperature, 74° C. for several weeks and its biological mitogenic activity is not altered by exposing it to ultra violet light overnight.

Cell growth factor, beta taipoxin, may be obtained essentially as a fraction of venom, from species of poisonous snake. Cell growth factor is preferably obtained from the venom of a species of Australian taipan snake, particularly the species *Oxyuranus s. scutellatus*.

The non-toxic beta taipoxin which is an active cell growth factor is obtained by separating the peptide fraction by, high pressure liquid chromatography, using ion exchange chromatography.

Fractionation of Venom: The active cell growth factor, a non-toxic beta taipoxin is preferably separated from fresh frozen venom, although lyophilized whole venom may also be used. The liquid venom is diluted 1:1 with 0,01 M phosphate buffer saline (PBS) and preferably centrifuged to sediment insoluble debris, which can also be removed by filtration. Typically, the diluted and centrifuged 50 mg venom is loaded on high pressure liquid chromatography, from Toso Co. Japan and the ion exchange column from Polymer Laboratories UK, maintained at 20° C. temperature. A plurality of fractions according to the relative ionic charge are eluted preferably, using gradient Trizma 2-amino-2-(hydroxymethyl)propane-1,3-diol-HCl buffer pH 7.3. The Toso high pressure liquid chromatography automatically mixes 1.0 molar Trizma-HCl buffer with water to yield gradient Trizma-HCl buffer from 0.01 molar to 1.0 molar. Any suitable gradient buffer may be used and Trizma-HCl buffer having pH 6.0 to 8.0 can be used.

BRIEF DESCRIPTION OF THE DRAWINGS:

The venom of *Oxyuranus s. scutellatus* resolved into 11 major fractions by high pressure liquid chromatography (FIG. No. 1). Fraction 6 represents the active cell growth factor of beta taipoxin. The fraction containing the mitogenic active peptide may be used in this form as a cell growth promoter, but may also be and preferably is further purified to obtain 100% purity to substantially remove mitogenic inactive substances as well. Preferably, the mitogenic active fraction 6 is concentrated and dialyzed simultaneously using dialysis apparatus from Spectrum Co., to $\frac{1}{20}^{th}$ volume and further purified by high pressure liquid chromatography as second run under identical conditions, such as gradient buffer temperature etc. The second time running of the concentrate of the cell growth factor fraction 6 resolved into one peak (FIG. No. 2). This peak material is sequenced for its first fifteen amino acids from the N-terminal SEQ ID No: 1 and was found to be exactly similar to beta taipoxin. FIG. No. 3 shows molecular weights on HPLC.

Initially each fraction was tested for the cell proliferative activity on rat adrenal pheochromocytoma, PC 12, cells in concentrations ranging from 5 μg/ml to 0.1 μg/ml. PC12 cells were maintained in Dulbecco Modified Eagle's Medium (DMEM) serum free medium and various concentrations of 11 fractions were added. The growth pattern of PC12 cells in presence of each fraction was compared to the cells maintained in DMEM containing 10% serum. All fractions showed toxic effect when the concentration of the fraction was greater than 1 μg/ml. However, fraction 6 of *Oxyuranus s. scutellatus* venom showed proliferative growth of PC12 cells at 1, 0.5 and 0.1 μg/ml concentration.

Figure 1:
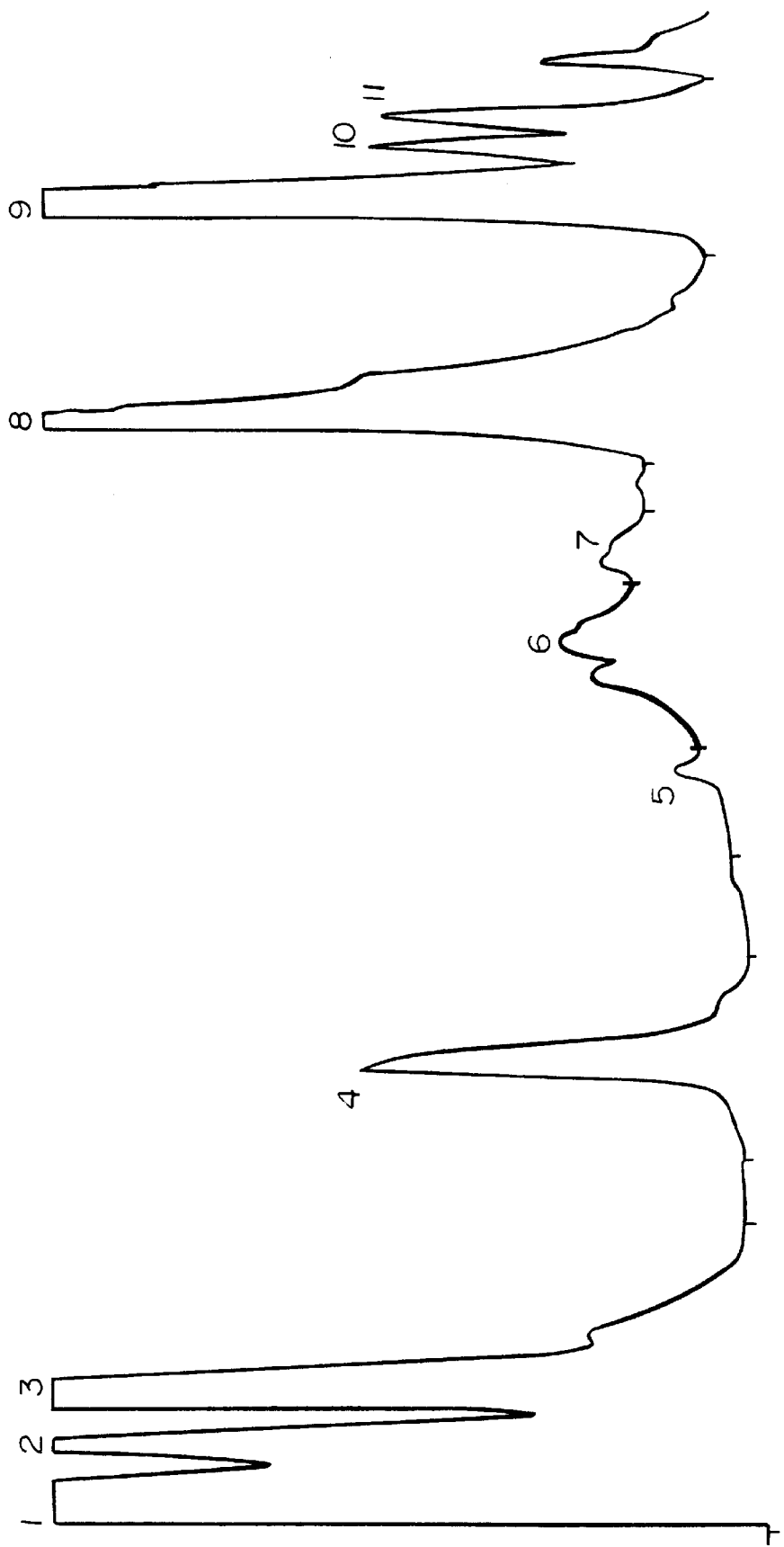
Figure 2:
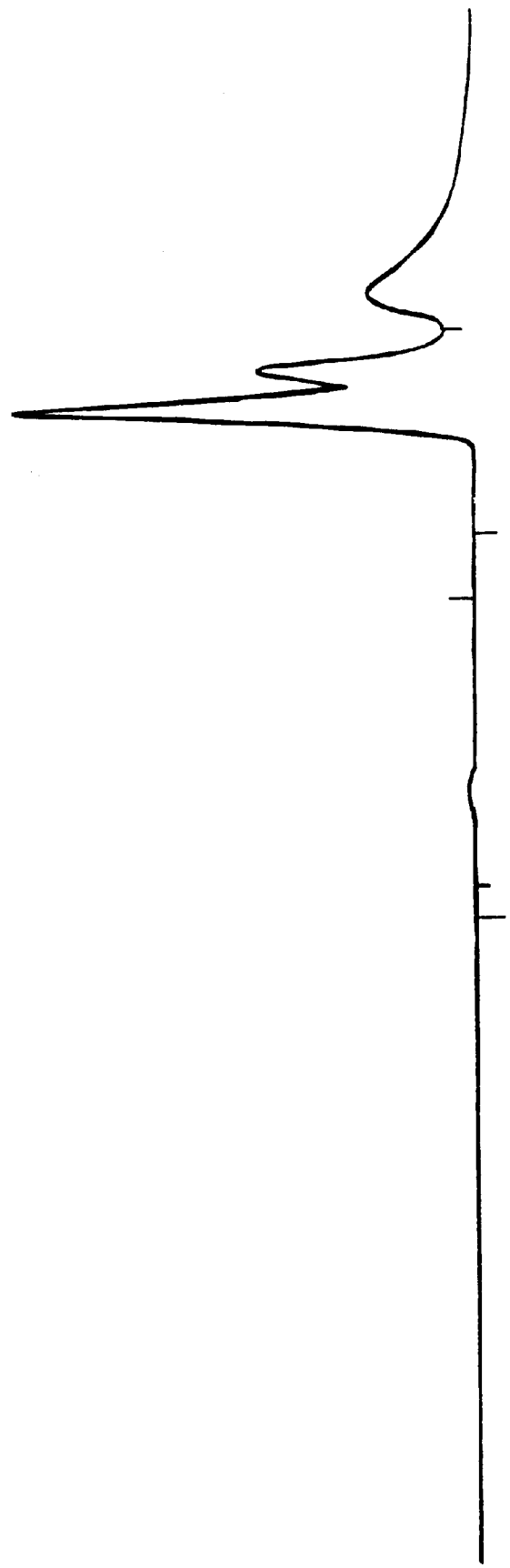
Figure 3:
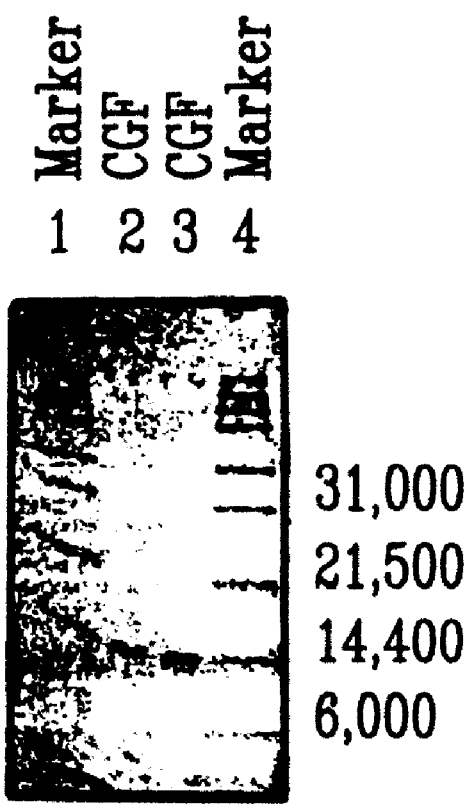

The proliferative of cell growth factor was studied on wide range of cells of primary and secondary cultures. The results on primary cell cultures are shown in table 1.

Growth stimulating effect of cell growth factor on primary cultures of mouse kidney and spleen cells versus conventional medium containing 10% FBS fetal bovine serum and serum free medium

TABLE 1

Growth stimulating effect of cell growth factor on primary cultures of mouse kidney and spleen cells versus conventional medium containing 10% FBS fetal bovine serum and serum free medium

|  | Mouse Kidney | | Mouse Spleen | |
| --- | --- | --- | --- | --- |
| Medium | 48 hours | 96 hours | 48 hours | 96 hours |
| 10% FBS | ++ | ++++ | — | ++ |
| no FBS | — | + | — | — |
| no FBS + 0.5 μg/ml CGF | +++ | ++++ | ++ | ++ |
| no FBS + 0.1 μg/ml CGF | ++ | ++++ | ++ | ++ |

++++ Confluent monolayer
++ 50% monolayer
+ 25% monolayer
— No growth

TABLE 2

Growth stimulating effect of cell growth factor on PC12 Cells*

|  | Incubation period | |
| --- | --- | --- |
| Medium | 48 hours | 96 hours |
| 10% FBS | 2.3 × 10$^5$ | 4.3 × 10$^5$ |
| Serum free | 1.0 × 10$^5$ | 0.6 × 10$^5$ |
| serum free + 5 μg/ml CGF | toxic | toxic |
| serum free + 1 μg/ml CGF | 1.9 × 10$^5$ | 2.1 × 10$^5$ |
| serum free + 0.5 μg/ml CGF | 2.3 × 10$^5$ | 4.0 × 10$^5$ |
| serum free + 0.1 μg/ml CGF | 2.4 × 10$^5$ | 4.3 × 10$^5$ |

*Initial cell count was 10$^5$ cells/ml

The concentration higher than 1 μg/ml of cell growth factor is toxic to PC12 cells. Therefore, concentrations ranging from 1 μg/ml to 0.01 μg/ml were used to screen other cell lines for mitogenic effects of cell growth factor. The addition of 0.1 μg/ml cell growth factor gives growth comparable to the medium containing 10% FBS, which proves its remarkable mitogenic property. The results are shown in table 3.

TABLE 3

Growth stimulating effect of cell growth factor on various established cell lines

|  | Serum free medium | | | |
| --- | --- | --- | --- | --- |
| Cell Line | none | 0.1 μg/ml | 0.5 μg/ml | 10% FBS |
| Chang's liver | retarded | normal | normal | normal |
| NIH 3T3 | retarded | normal | normal | normal |
| Skin | no growth | normal | normal | normal |
| NS-20 | retarded | normal | normal | normal |
| PC-12 | retarded | neurite | neurite | normal |
| SP/2 | no growth | no growth | no growth | normal |

The results show that cell growth factor is mitogenic for most of the cells tested. Cell growth factor seems to be neurotrophic as PC12 cells show neurite outgrowth in the presence of this growth factor.

Experimental cuts were made on both hips of test mice. The right cuts were treated with cell growth factor and the left with PBS. The cuts treated with cell growth factor healed much faster.

A friend, experienced a deep wound on the top of his foot, which showed non closure after 3 months and was deemed to be chronic. After applying cell growth factor, twice a day, his wound began to heal. He experienced the effect of cell growth factor within 24 hours. Therefore, cell growth factor can be a wound healer.

Cell growth factor is stable at 4° C. for a long period of time. Cell growth factor is non-toxic, when 50 μg in 0.5 ml phosphorate buffer saline is injected intraperitoneally in a 20 gram mouse. Being a cell growth promoter having a neurotrophic activity, this cell growth factor will be an excellent wound and burn healer.

The cell growth factor is beta taipoxin of the present invention is a particularly effective mitogenic agent. Since it is substantially free of toxic activity, the cell growth factor can be used to grow wide range of cells in the serum free medium. Further, it may be used for a rapid proliferation of cells either for research or for production purposes, also in the case of dermal monolayers to grow in vitro for the treatment of burn victims and for wound healing.

It is further believed that cell growth factor, which is a beta taipoxin, and its method of preparation of the present invention has utility for treating burns and wounds including chronic wounds. Generally, the healing effects is accomplished by treating the wounds or cuts with cell growth factor having 100 μg/ml protein concentration in PBS in liquid form. It can be used after mixing with silvadene or any other appropriate ointment. The application of cell growth factor once or twice a day on the afflicted area, followed by dressing with silvadeen, the healing effect starts within 24 hours. Moreover, after the wound is healed, no scar is produced because the hard dead tissue on the wound sloughs off as a effect of cell growth factor.

Analysis of the cell growth factor active peptide: The concentrated fraction number 6 which was obtained by initial fractionating the crude venom, resolved into a single peak on second time fractionation on high pressure liquid chromatography under identical conditions. The peak material was estimated to have a molecular weight in the vicinity of 14,000 daltons, when compared with Novex protein markers lysozyme, and trypsin inhibitor, having molecular weights 14,400 and 21,500 daltons respectively on 14% precast gel (FIG. No. 3).

REFERENCES

1. J. Fohlman, D. Eaker, E. Karlsson and S. Thesleff.
   Eur. J. Biochem 68, 457–469 (1976).
2. Lind P.
   Eur. J. Biochen. 128, 7175 (1982).
3. Crosland, R. D.
   Toxicon 27, 655663 (1989).
4. Crosland, R. D.
   Toxicon 29, 613631 (1991).
5. Simpson, L. L. et al.
   Toxicon 31, 1326 (1993).
6. A. Buckley, J. M. Davidson, C. D. Kamerath, T. B. Wolt and S. C. Woodward
   Proc. Natl Acad Sci. USA 82, 73407344, (1985).
7. A. Wells, J. B. Welsh, C. S. Lazar, H. S. Wiley, G. N. Gili and M. G. Rosenfeld
   Science, 247, 962964, (1990).
8. G. S. Schultz et al.
   Science, 235, 350352, (1987).
9. J. F. Rubin et al.
   Proc. Natl. Acad. Sci. USA 86, 802806, (1989).
10. G. L. Brown, etal.
    J. Exp. Med. The Rockefeller University Press, 163, 13191324, (1986).

```
                        SEQUENCE LISTING (1) GENERAL INFORMATION:

(iii) NUMBER OF SEQUENCES:1

(2) INFORMATION FOR SEQ ID NO:1:

(i) SEQUENCE CHARACTERISTICS:
        (A) LENGTH:15

(B) TYPE:AMINO ACID (C) STRANDEDNESS: SINGLE (D) TOPOLOGY:LINEAR (ii) MOLECULE TYPE: (PROTEIN) IN SEQ ID NO: 1

(iii) HYPOTHETICAL:NO (iv) ANTI-SENSE: NO (v) FRAGMENT TYPE:N (vi) ORIGINAL SOURCE: (SNAKE VENOM): SEQ ID NO: 1:
         (A) ORGANISM: (AUSTRALIAN TAIPAN)

(B) STRAIN:WILD (C) INDIVIDUAL ISOLATE:AUSTRALIA WILD (D) DEVELOPMENTAL STAGE:ADULT (E) HAPLOTYPE:

(F) TISSUE TYPE:

(G) CELL TYPE:

(H) CELL LINE:

(I ) ORGANELLE:

(vii) IMMEDIATE SOURCE: (SNAKE VENOM) SEQ ID NO: 1:
          (A) LIBRARY:

(B) CLONE:

(x) PUBLICATION INFORMATION:
         (A) AUTHORS:

(B) TITLE:
```

-continued

```
(C) JOURNAL:

(D) VOLUME:

(E) ISSUE:

(F) PAGES:

(G) DATE:

(xi) SEQUENCE DESCRIPTION: SEQ ID NO: 1:

ASN LEU VAL GLU PHE GLY LYS MET ILE GLU
 1              5                  10

CYS ALA ILE ARG ASN
                15
```

What is claimed is:

1. A method for treating a wound comprising treating said wound with a composition comprising a cell growth factor, wherein the cell growth factor consists essentially of a peptide, wherein the first 15 amino acids from the N-terminus of said peptide are identified in SEQ ID No: 1.

2. A method as in claim 1 wherein the wound is a cut.

3. A method as in claim 1 wherein the wound is a burn.

4. A method as in claim 1 wherein the wound is an abrasion.

5. A method as in claim 1 wherein the treatment comprises applying a composition containing the peptide to the wound.

6. A method as in claim 5 wherein the composition comprises an ointment containing about 100 μg/ml of beta taipoxin.

7. A method as in claim 5 wherein the peptide consists essentially of beta taipoxin and has a molecular weight of approximately 14,000 daltons.

8. An ointment comprising a cell growth factor, wherein the cell growth factor consists essentially of a peptide, wherein the first 15 amino acids from the N-terminus of said peptide are identified in SEQ ID No: 1.

9. An ointment as in claim 8 wherein the peptide consists essentially of beta taipoxin obtained from snake venom.

* * * * *